US008613230B2

(12) United States Patent
Blumenkranz et al.

(10) Patent No.: US 8,613,230 B2
(45) Date of Patent: Dec. 24, 2013

(54) FORCE SENSING FOR SURGICAL INSTRUMENTS

(71) Applicant: Intuitive Surgical Operations, Inc., Sunnyvale, CA (US)

(72) Inventors: Stephen J. Blumenkranz, Los Altos Hills, CA (US); David Q. Larkin, Menlo Park, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 0 days.

(21) Appl. No.: 13/735,335

(22) Filed: Jan. 7, 2013

(65) Prior Publication Data

US 2013/0165869 A1  Jun. 27, 2013

Related U.S. Application Data

(63) Continuation of application No. 11/864,974, filed on Sep. 29, 2007, now Pat. No. 8,375,808, which is a continuation-in-part of application No. 11/537,241, filed on Sep. 29, 2006.

(60) Provisional application No. 60/755,108, filed on Dec. 30, 2005.

(51) Int. Cl.
G01L 1/22 (2006.01)
(52) U.S. Cl.
USPC .................................................. 73/862.044
(58) Field of Classification Search
USPC .................................................. 73/862.044
See application file for complete search history.

(56) References Cited

U.S. PATENT DOCUMENTS

| 3,515,137 | A | * | 6/1970 | Santomieri | 604/165.02 |
| 4,838,280 | A | * | 6/1989 | Haaga | 600/564 |
| 4,906,907 | A | | 3/1990 | Tsuchihashi et al. | |
| 5,631,973 | A | | 5/1997 | Green | |
| 5,779,697 | A | * | 7/1998 | Glowa et al. | 606/185 |
| 5,784,542 | A | | 7/1998 | Ohm et al. | |
| 5,807,326 | A | | 9/1998 | Oneill et al. | |
| 5,807,377 | A | | 9/1998 | Madhani et al. | |
| 6,120,433 | A | | 9/2000 | Mizuno et al. | |
| 6,331,181 | B1 | | 12/2001 | Tierney et al. | |
| 6,344,038 | B1 | | 2/2002 | Weber | |
| 6,371,952 | B1 | | 4/2002 | Madhani et al. | |

(Continued)

FOREIGN PATENT DOCUMENTS

EP  1650615 A1  4/2006
FR  2693397 A1  1/1994

(Continued)

OTHER PUBLICATIONS

Cepolina F. et al., "Review of robotic fixtures for minimally invasive surgery," International Journal of Medical Robotics and Computer Assisted Surgery, 2004, pp. 43-63, vol. 1, Issue-1.

(Continued)

Primary Examiner — Lisa Caputo
Assistant Examiner — Octavia Davis-Hollington

(57) ABSTRACT

An apparatus, system, and method for improving force and torque sensing and feedback to the surgeon performing a telerobotic surgery are provided. In one embodiment, a surgical instrument, a robotic surgical system, a cannula, a cannula seal, and a method for improved sensing of z-axis forces on a robotic surgical instrument are disclosed.

16 Claims, 17 Drawing Sheets

(56) References Cited

U.S. PATENT DOCUMENTS

| | | |
|---|---|---|
| 6,470,205 B2 | 10/2002 | Bosselmann et al. |
| 6,491,701 B2 | 12/2002 | Tierney et al. |
| 6,494,882 B1 | 12/2002 | Lebouitz et al. |
| 6,574,355 B2 | 6/2003 | Green |
| 6,587,750 B2 | 7/2003 | Gerbi et al. |
| 6,594,552 B1 | 7/2003 | Nowlin et al. |
| 6,676,684 B1 | 1/2004 | Morley et al. |
| 6,770,081 B1 | 8/2004 | Cooper et al. |
| 6,783,524 B2 | 8/2004 | Anderson et al. |
| 6,817,974 B2 | 11/2004 | Cooper et al. |
| 6,835,173 B2 | 12/2004 | Couvillon, Jr. |
| 6,866,671 B2 | 3/2005 | Tierney et al. |
| 6,879,880 B2 | 4/2005 | Nowlin et al. |
| 6,902,560 B1 | 6/2005 | Morley et al. |
| 6,936,042 B2 | 8/2005 | Wallace et al. |
| 7,357,774 B2 | 4/2008 | Cooper |
| 7,606,615 B2 | 10/2009 | Makower et al. |
| 7,648,513 B2 | 1/2010 | Green et al. |
| 7,678,075 B2 | 3/2010 | Wantink et al. |
| 7,824,401 B2 | 11/2010 | Manzo et al. |
| 7,842,028 B2 | 11/2010 | Lee |
| 8,004,229 B2 | 8/2011 | Nowlin et al. |
| 2002/0111635 A1 | 8/2002 | Jensen et al. |
| 2002/0133174 A1 | 9/2002 | Charles et al. |
| 2003/0036748 A1 | 2/2003 | Cooper et al. |
| 2003/0229286 A1 | 12/2003 | Lenker |
| 2005/0021050 A1 | 1/2005 | Cooper |
| 2005/0200324 A1 | 9/2005 | Guthart et al. |
| 2006/0161136 A1 | 7/2006 | Anderson et al. |
| 2006/0161137 A1 | 7/2006 | Orban, III |
| 2006/0161138 A1 | 7/2006 | Orban, III |
| 2006/0235436 A1 | 10/2006 | Anderson et al. |
| 2007/0119274 A1 | 5/2007 | Devengenzo et al. |
| 2007/0137371 A1 | 6/2007 | Devengenzo et al. |
| 2007/0151390 A1 | 7/2007 | Blumenkranz et al. |
| 2007/0151391 A1 | 7/2007 | Larkin et al. |
| 2007/0156019 A1 | 7/2007 | Larkin et al. |
| 2008/0065111 A1 | 3/2008 | Blumenkranz et al. |

FOREIGN PATENT DOCUMENTS

| | | |
|---|---|---|
| JP | 9318469 A | 12/1997 |
| JP | 2002159509 A | 6/2002 |
| JP | 27167644 A2 | 7/2007 |
| WO | 2005039835 A1 | 5/2005 |
| WO | 2007120329 A2 | 10/2007 |

OTHER PUBLICATIONS

PCT/US06/61994 International Search Report and Written Opinion of the International Searching Authority, mailed Oct. 17, 2007, 9 pages.

PCT/US08/76123 International Search Report and Written Opinion of the International Search Authority, mailed May 19, 2009, 15 pages.

PCT/US08/76123 Partial International Search Report, mailed Jan. 12, 2009, 3 pages.

Seibold, Ulrich et al., "A 6-axis force/torque sensor design for haptic feedback in minimally invasive robotic surgery," In: Proceedings of the 2nd VDE World Microtechnologies, 2003, 6 pages.

U.S. Appl. No. 60/752,755, filed Dec. 20, 2005; Devengenzo, Roman L. et al.

U.S. Appl. No. 60/755,108, filed Dec. 30, 2005, Blumenkranz, Stephen J. et al.

U.S. Appl. No. 60/755,157, filed Dec. 30, 2005, Larkin, David Q.

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

\* cited by examiner

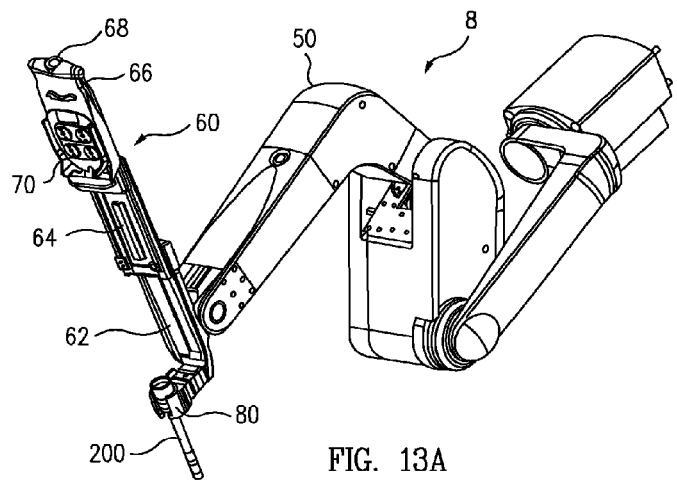 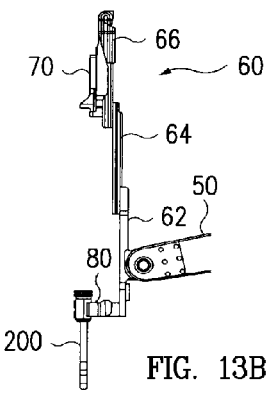
FIG. 13A  FIG. 13B
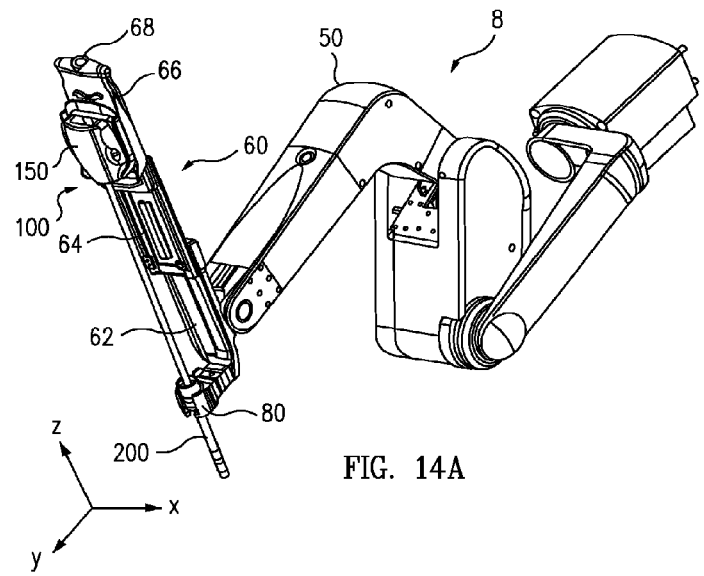 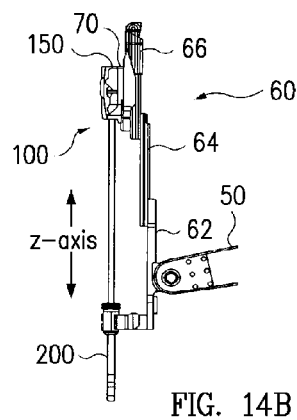
FIG. 14A  FIG. 14B

FORCE SENSING FOR SURGICAL INSTRUMENTS

CROSS-REFERENCE TO RELATED APPLICATIONS AND PATENTS

This application is a continuation of U.S. patent application Ser. No. 11/864,794 (filed Sep. 29, 2007), which is a continuation-in-part of U.S. patent application Ser. No. 11/537,241 (filed Sep. 29, 2006), which claims priority to and the benefit of U.S. Patent Application No. 60/755,108 (filed Dec. 30, 2005), the full disclosures of which are incorporated by reference herein for all purposes.

This application is related to U.S. patent application Ser. No. 11/093,372 filed Mar. 30, 2005 (US20050200324 A1, published Sep. 15, 2005), and U.S. Pat. Nos. 6,936,042, 6,902,560, 6,879,880, 6,866,671, 6,817,974, 6,783,524, 6,676,684, 6,371,952, 6,331,181, and 5,807,377, the full disclosures of which are incorporated by reference herein for all purposes.

TECHNICAL FIELD

The present invention relates generally to surgical robot systems and, more particularly, to a system and method for sensing forces applied to a surgical instrument.

BACKGROUND

In robotically-assisted surgery, the surgeon typically operates a master controller to control the motion of surgical instruments at the surgical site from a location that may be remote from the patient (e.g., across the operating room, in a different room or a completely different building from the patient). The master controller usually includes one or more hand input devices, such as handheld wrist gimbals, joysticks, exoskeletal gloves, handpieces or the like, which are operatively coupled to the surgical instruments through a controller with servo motors for articulating the instruments' position and orientation at the surgical site. The servo motors are typically part of an electromechanical device or surgical manipulator arm ("the slave") that includes a plurality of joints, linkages, etc., that are connected together to support and control the surgical instruments that have been introduced directly into an open surgical site or through trocar sleeves inserted through incisions into a body cavity, such as the patient's abdomen. Depending on the surgical procedure, there are available a variety of surgical instruments, such as tissue graspers, needle drivers, electrosurgical cautery probes, etc., to perform various functions for the surgeon, e.g., retracting tissue, holding or driving a needle, suturing, grasping a blood vessel, or dissecting, cauterizing or coagulating tissue. A surgeon may employ a large number of different surgical instruments/tools during a procedure.

This new method of performing telerobotic surgery through remote manipulation has created many new challenges. One such challenge is providing the surgeon with the ability to accurately "feel" the tissue that is being manipulated by the surgical instrument via the robotic manipulator. The surgeon must rely on visual indications of the forces applied by the instruments or sutures. It is desirable to sense the forces and torques applied to the tip of the instrument, such as an end effector (e.g., jaws, grasper, blades, etc.) of robotic endoscopic surgical instruments, in order to feed the forces and torques back to the surgeon user through the system hand controls or by other means such as visual display or audible tone. One device for this purpose from the laboratory of G. Hirzinger at DLR Institute of Robotics and Mechatronics is described in "Review of Fixtures for Low-Invasiveness Surgery" by F. Cepolina and R C Michelini, *Int'l Journal of Medical Robotics and Computer Assisted Surgery*, Vol. 1, Issue 1, page 58, the contents of which are incorporated by reference herein for all purposes. However, that design disadvantageously places a force sensor distal to (or outboard of) the wrist joints, thus requiring wires or optic fibers to be routed through the flexing wrist joint and also requiring the yaw and grip axes to be on separate pivot axes.

Another problem has been fitting and positioning the necessary wires for mechanical actuation of end effectors in as small a space as possible because relatively small instruments are typically desirable for performing surgery.

What is needed, therefore, are improved telerobotic systems and methods for remotely controlling surgical instruments at a surgical site on/in a patient. In particular, these systems and methods should be configured to provide accurate feedback of forces and torques to the surgeon to improve user awareness and control of the instruments.

SUMMARY

The present invention provides an apparatus, system, and method for improving force and torque feedback to and sensing by the surgeon performing a telerobotic surgery. In particular, a surgical instrument, a robotic surgical system, a cannula, a cannula seal, and a method for improved sensing of z-axis forces on a robotic surgical instrument are disclosed.

Advantageously, the present invention provides for reducing friction to substantially reduce noise or other interference when determining z-axis forces from outside the body.

The scope of the invention is defined by the claims, which are incorporated into this section by reference. A more complete understanding of embodiments of the present invention will be afforded to those skilled in the art, as well as a realization of additional advantages thereof, by a consideration of the following detailed description of one or more embodiments. Reference will be made to the appended sheets of drawings that will first be described briefly.

BRIEF DESCRIPTION OF THE DRAWINGS

FIGS. 10-14B are perspective views and respective side views of a manipulator, including the coupling of a cannula and an instrument in FIGS. 12A-12B and 14A-14B, in accordance with an embodiment of the present invention.

Figure 1A:
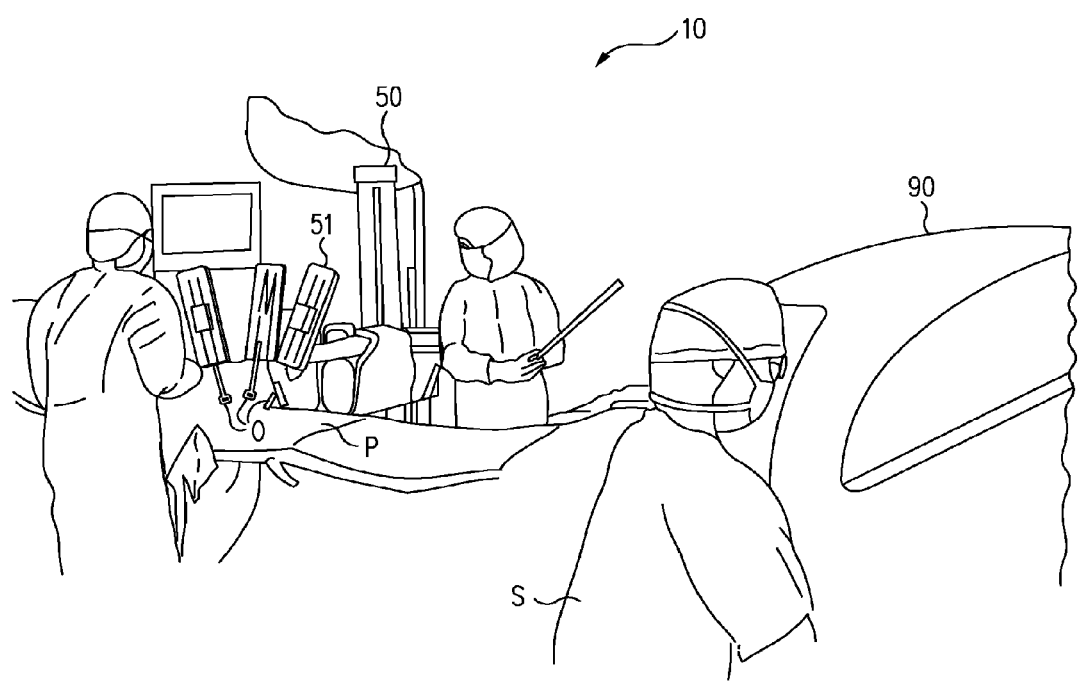
FIG. 1A is a perspective view of a robotic surgical system in accordance with an embodiment of the present invention.

Embodiments of the present invention and their advantages are best understood by referring to the detailed description that follows. It should be appreciated that like reference numerals are used to identify like elements illustrated in one or more of the figures. It should also be appreciated that the figures may not be necessarily drawn to scale.

DETAILED DESCRIPTION

The present invention provides a multi-component system, apparatus, and method for sensing forces applied to tissue while performing robotically-assisted surgical procedures on a patient, particularly including open surgical procedures, neurosurgical procedures, and endoscopic procedures, such as laparoscopy, arthroscopy, thoracoscopy, and the like. The system and method of the present invention are particularly useful as part of a telerobotic surgical system that allows the surgeon to manipulate the surgical instruments through a servomechanism from a remote location from the patient. To that end, the manipulator apparatus or slave of the present invention will usually be driven by a kinematically-equivalent master having six or more degrees of freedom (e.g., 3 degrees of freedom for position and 3 degrees of freedom for orientation) to form a telepresence system with force reflection. A description of a suitable slave-master system can be found in U.S. Pat. No. 6,574,355, the complete disclosure of which is incorporated herein by reference for all purposes.

Figure 1B:
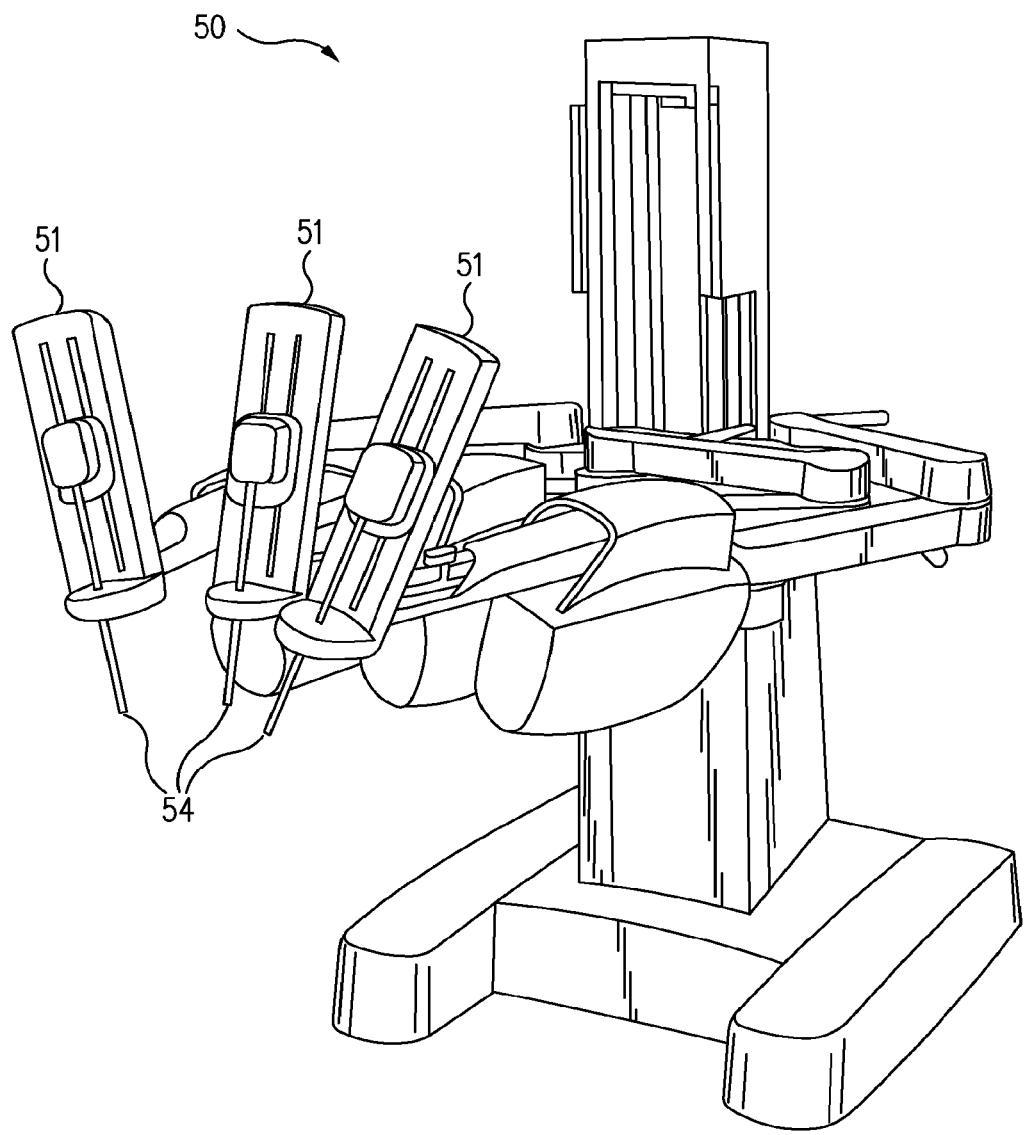
FIG. 1B is a perspective view of a robotic surgical arm cart system of the robotic surgical system in FIG. 1A in accordance with an embodiment of the present invention.
Figure 1C:
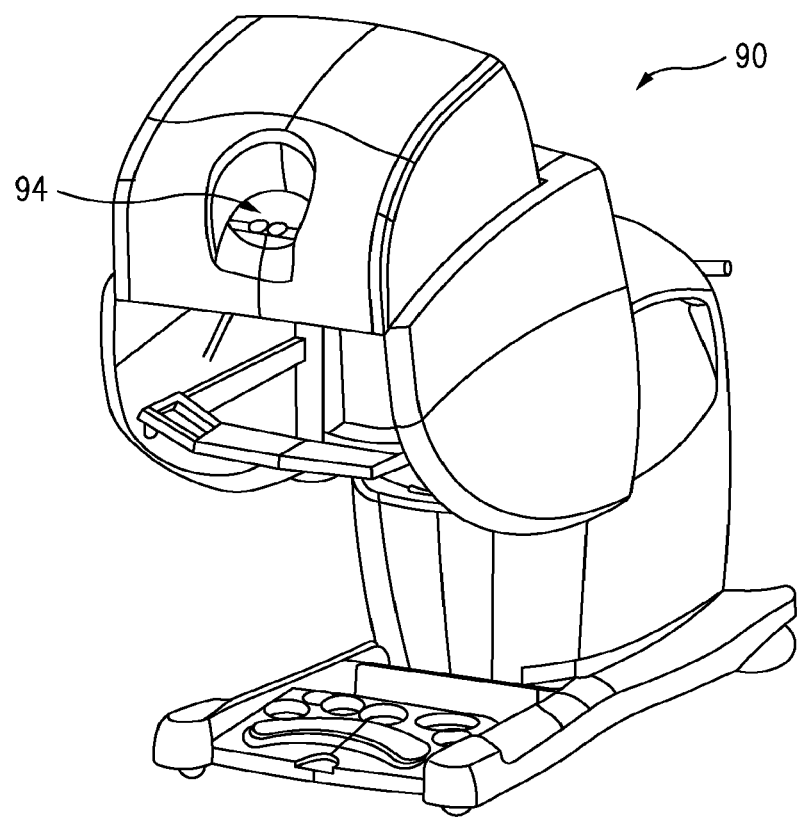
FIG. 1C is a front perspective view of a master console of the robotic surgical system in FIG. 1A in accordance with an embodiment of the present invention.

Referring to the drawings in detail, wherein like numerals indicate like elements, a robotic surgical system 10 is illustrated according to an embodiment of the present invention. As shown in FIGS. 1A through 1C, robotic system 10 generally includes one or more surgical manipulator assemblies 51 mounted to or near an operating table and a master control assembly 90 for allowing the surgeon S to view the surgical site and to control the manipulator assemblies 51. The system 10 will also include one or more viewing scope assemblies and a plurality of surgical instrument assemblies 54 adapted for being removably coupled to the manipulator assemblies 51 (discussed in more detail below). Robotic system 10 includes at least two manipulator assemblies 51 and preferably at least three manipulator assemblies 51. The exact number of manipulator assemblies 51 will depend on the surgical procedure and the space constraints within the operating room, among other factors. As discussed in detail below, one of the assemblies 51 will typically operate a viewing scope assembly (e.g., in endoscopic procedures) for viewing the surgical site, while the other manipulator assemblies 51 operate surgical instruments 54 for performing various procedures on the patient P.

Control assembly 90 may be located at a surgeon's console which is usually located in the same room as operating table O so that the surgeon may speak to his/her assistant(s) and directly monitor the operating procedure. However, it should be understood that the surgeon S can be located in a different room or a completely different building from the patient P. Master control assembly 90 generally includes a support, a monitor for displaying an image of the surgical site to the surgeon S, and one or more master(s) for controlling manipulator assemblies 51. Master(s) may include a variety of input devices, such as hand-held wrist gimbals, joysticks, gloves, trigger-guns, hand-operated controllers, voice recognition devices, or the like. Preferably, master(s) will be provided with the same degrees of freedom as the associated surgical instrument assemblies 54 to provide the surgeon with telepresence, the perception that the surgeon is immediately adjacent to and immersed in the surgical site, and intuitiveness, the perception that the master(s) are integral with the instruments 54 so that the surgeon has a strong sense of directly and intuitively controlling instruments 54 as if they are part of his or her hands. Position, force, and tactile feedback sensors (not shown) may also be employed on instrument assemblies 54 to transmit position, force, and tactile sensations from the surgical instrument back to the surgeon's hands as he/she operates the telerobotic system. One suitable system and method for providing telepresence to the operator is described in U.S. Pat. No. 6,574,355, which has previously been incorporated herein by reference.

The monitor 94 will be suitably coupled to the viewing scope assembly such that an image of the surgical site is provided adjacent the surgeon's hands on surgeon console. Preferably, monitor 94 will display an image on a display that is oriented so that the surgeon feels that he or she is actually looking directly down onto the operating site. To that end, an image of the surgical instruments 54 appears to be located substantially where the operator's hands are located even though the observation points (i.e., the endoscope or viewing camera) may not be from the point of view of the image. In addition, the real-time image is preferably transformed into a stereo image such that the operator can manipulate the end effector and the hand control as if viewing the workspace in substantially true presence. By true presence, it is meant that the presentation of an image is a true stereo image simulating the viewpoint of an operator that is physically manipulating the surgical instruments 54. Thus, a controller (not shown) transforms the coordinates of the surgical instruments 54 to a perceived position so that the stereo image is the image that one would see if the camera or endoscope was located directly behind the surgical instruments 54. A suitable coordinate transformation system for providing this virtual image is described in U.S. patent application Ser. No. 08/239,086, filed May 5, 1994, now U.S. Pat. No. 5,631,973, the complete disclosure of which is incorporated herein by reference for all purposes.

A servo control is provided for transferring the mechanical motion of masters to manipulator assemblies 51. The servo control may be separate from, or integral with, manipulator assemblies 51. The servo control may provide force and torque feedback from the surgical instruments 51 to the hand-operated masters. In addition, the servo control may include a safety monitoring controller (not shown) to safely halt system operation, or at least inhibit all robot motion, in response to recognized undesirable conditions (e.g., exertion of excessive force on the patient, mismatched encoder readings, etc.). The servo control preferably has a servo bandwidth with a 3 dB cut off frequency of at least 10 Hz so that the system can quickly and accurately respond to the rapid hand motions used by the surgeon and yet to filter out undesirable surgeon hand tremors. To operate effectively with this system, manipulator assemblies 51 have a relatively low inertia, and the drive motors have relatively low ratio gear or pulley couplings. Any suitable conventional or specialized servo control may be used in the practice of the present invention, with those incorporating force and torque feedback being particularly preferred for telepresence operation of the system.

Referring now to FIGS. 2-6 in conjunction with FIGS. 1A-1C, an improved apparatus, system, and method for sensing and feedback of forces and/or torques to the surgeon will be described in accordance with an embodiment of the present invention.

Figure 2:
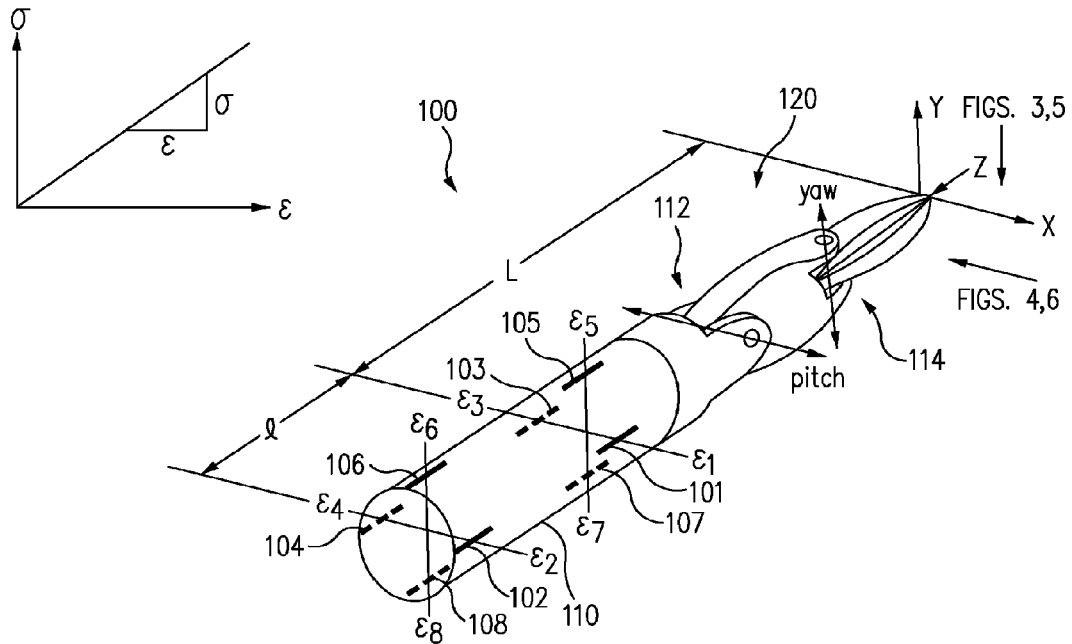
FIG. 2 is a perspective view of a surgical instrument distal end showing a wrist, grip jaws, and force sensors for use with a telerobotic surgical system in accordance with an embodiment of the present invention.

FIG. 2 shows a perspective view of a portion 100 of a surgical instrument that includes a shaft 110, wrist joints 112 and 114, and an end portion 120 that may be used to manipulate a surgical tool and/or contact the patient. The surgical instrument also includes a housing 150 (FIGS. 9A-9C) that operably interfaces with a robotic manipulator arm, in one embodiment via a sterile adaptor interface. Applicable housings, sterile adaptor interfaces, and manipulator arms are disclosed in U.S. patent application Ser. No. 11/314,040 filed on Dec. 20, 2005, and U.S. application Ser. No. 11/613,800 filed on Dec. 20, 2006, the full disclosures of which are incorporated by reference herein for all purposes. Examples of applicable shafts, end portions, housings, sterile adaptors, and manipulator arms are manufactured by Intuitive Surgical, Inc. of Sunnyvale, Calif.

In a preferred configuration, end portion 120 has a range of motion that includes pitch and yaw motion about the x- and y-axes and rotation about the z-axis (as shown in FIG. 2). These motions, as well as actuation of an end effector, are done via cables running through shaft 110 and housing 150 that transfer motion from the manipulator arm 51. Embodiments of drive assemblies, arms, forearm assemblies, adaptors, and other applicable parts are described for example in U.S. Pat. Nos. 6,331,181, 6,491,701, and 6,770,081, the full disclosures of which are incorporated herein by reference for all purposes.

It is noted that various surgical instruments may be improved in accordance with the present invention, including but not limited to tools with and without end effectors, such as jaws, scissors, graspers, needle holders, micro-dissectors, staple appliers, tackers, suction irrigation tools, clip appliers, cutting blades, irrigators, catheters, and suction orifices. Alternatively, the surgical instrument may comprise an electrosurgical probe for ablating, resecting, cutting or coagulating tissue. Such surgical instruments are commercially available from Intuitive Surgical, Inc. of Sunnyvale, Calif.

In accordance with an embodiment of the present invention, instrument portion 100 includes sensors (e.g., strain gauges) mounted onto the exterior surface of shaft 110, oriented parallel to the longitudinal (lengthwise) axis of the shaft, termed the z-axis. The two axes perpendicular to the shaft are called the x- and y-axes. The signals from the sensors are combined arithmetically in various sums and differences (as will be explained in further detail below) to obtain measures of three perpendicular forces (e.g., $F_x$, $F_y$, and $F_z$) exerted upon the instrument tip and the torques (Tx, Ty) about the two axes perpendicular to the shaft axis (i.e., the x- and y-axes). In accordance with the present invention, the measurement of the forces is made independent of the orientation and effective lever arm length of a wrist mechanism at the distal end of the instrument. Forces exerted against end portion 120 are detected by the force sensing elements, which may be operably coupled to servo control via an interrogator or a processor for transmitting these forces to master(s).

In one embodiment, eight strain gauges 101, 102, 103, 104, 105, 106, 107, and 108 are mounted to the outer surface of shaft 110 or in shallow recesses near the outer surface and provide strain data $\epsilon_1$, $\epsilon_2$, $\epsilon_3$, $\epsilon_4$, $\epsilon_5$, $\epsilon_6$, $\epsilon_7$, and $\epsilon_8$, respectively. The primary strain sensing direction of the gauges are oriented parallel to the z-axis. The gauges are mounted in two groups of four, wherein the four gauges in one group are spaced equally, 90 degrees apart around the circumference of the shaft at one axial position (i.e., forming two "rings" of four strain gauges each). One group of four (e.g., gauges 101, 103, 105, and 107) is mounted proximal to a wrist mechanism as close to a distal end of shaft 110 as possible. The second group of four (e.g., gauges 102, 104, 106, and 108) is mounted at a chosen distance "l" from the first group of four (toward a proximal end of shaft 110) and aligned with them so that pairs of gauges in the two groups are aligned with each other (i.e., gauges 101 and 102, 103 and 104, 105 and 106, and 107 and 108 are aligned).

The z-axis force ($F_z$) including both surgical forces and wrist cable forces is found from the sum of the eight gauge outputs multiplied by a factor of EA/8, where E is the shaft material modulus of elasticity in the z-axis direction, and A is the cross-sectional area of the shaft. The lateral forces along the x- and y-axes ($F_x$ and $F_y$) at or near the tip are found from the difference of the gauge outputs of a pair of gauges on opposite sides of the shaft and the difference between the pair differences along the shaft multiplied by a factor of EI/2r1, where E is the shaft material modulus of elasticity in the z-axis direction, I is the shaft section moment of inertia, r is the radius from the shaft axis to the acting plane of the gauges, and 1 is the distance between the 2 groups of 4 gauges The calculations of the forces are derived from the following equations.

With respect to FIG. 2, $$E = \sigma/\epsilon$$

$$A = \pi(r_o^2 - r_i^2)$$

$$I = (\pi/4)(r_o^4 - r_i^4)$$

$$\sigma = (F/A) + (Mr/I)$$

$$\epsilon = [\epsilon_1\ \epsilon_2\ \epsilon_3\ \epsilon_4\ \epsilon_5\ \epsilon_6\ \epsilon_7\ \epsilon_8]$$

$$\begin{array}{ccc} F_x & F_y & F_z \\ \begin{bmatrix} 1 \\ -1 \\ -1 \\ 1 \\ 0 \\ 0 \\ 0 \\ 0 \end{bmatrix} EI/2lr & \begin{bmatrix} 0 \\ 0 \\ 0 \\ 0 \\ 1 \\ -1 \\ -1 \\ 1 \end{bmatrix} EI/2lr & \begin{bmatrix} 1 \\ 1 \\ 1 \\ 1 \\ 1 \\ 1 \\ 1 \\ 1 \end{bmatrix} - EA/8 \end{array}$$

Figure 3:
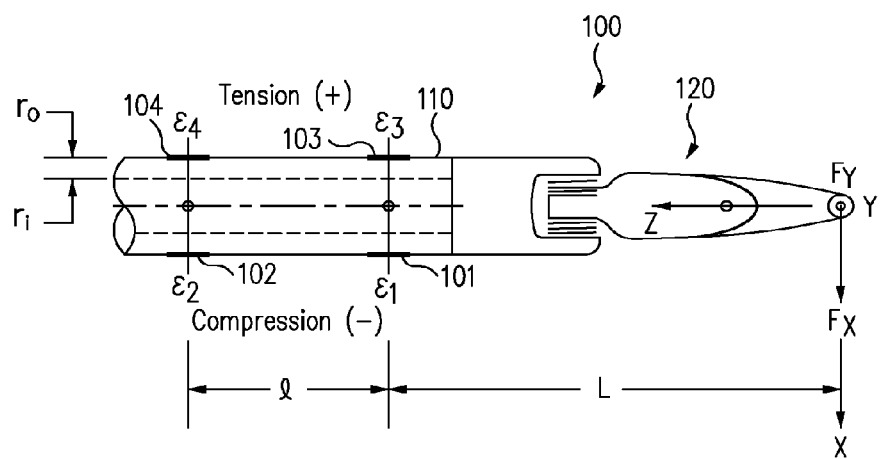
FIG. 3 is a first top view of the surgical instrument of FIG. 2 showing applied forces in accordance with the embodiment of the present invention.
Figure 4:
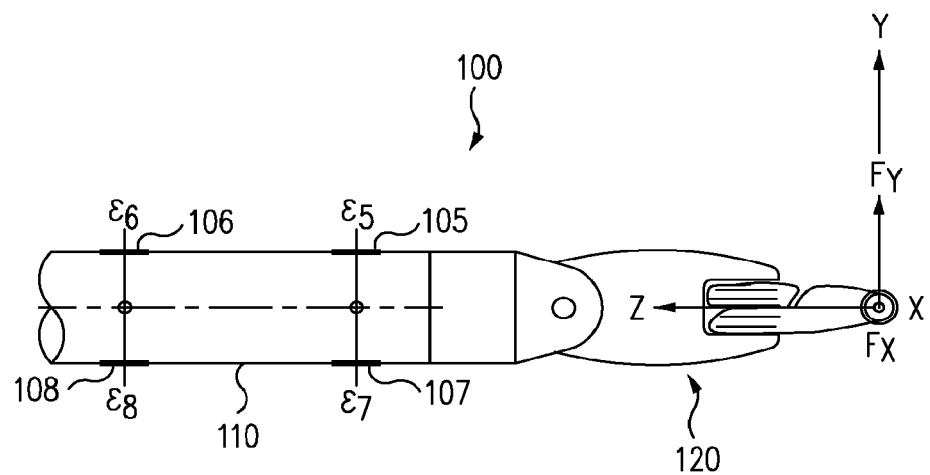
FIG. 4 is a first side view of the surgical instrument of FIG. 2 showing applied forces in accordance with the embodiment of the present invention.

With respect to FIGS. 3 and 4, $$A=(r_o^2-r_i^2)$$

$$I=(\pi/4)(r_0^4-r_i^4)$$

$$\sigma=Mr/I$$

$$\sigma_1=FLr/I$$

$$\sigma_2=F(L+1)r/I$$

$$E=\sigma/\epsilon => \epsilon=\sigma/E$$

$$\epsilon_1=-F_xLr/EI$$

$$\epsilon_2=-F_x(L+1)r/EI$$

$$\epsilon_2-\epsilon_1=-F_x 1 r/EI$$

$$\epsilon_4-\epsilon_3=F_x 1 r/EI$$

$$(\epsilon_4-\epsilon_3)-(\epsilon_2-\epsilon_1)=2F_x 1 r/EI$$

Thus, $$(\epsilon_1-\epsilon_2-\epsilon_3+\epsilon_4)EI/21r=F_x$$

$$(\epsilon_5-\epsilon_6-\epsilon_7+\epsilon_8)EI/21r=F_y$$

$$(\epsilon_1+\epsilon_2+\epsilon_3+\epsilon_4+\epsilon_5+\epsilon_6+\epsilon_7+\epsilon_8)EA/8=F_z$$

$F_x$ and $F_y$ are thus invariant with respect to L and invariant with respect to temperature at steady state.

Advantageously, the present invention makes the measured transverse forces (Fx, Fy) at the instrument tip independent of variations in the effective lever arm length due to wrist orientation changes or gripping position changes in the end portion during surgery. The measured transverse forces are also made independent of changes in the z-axis forces especially those due to the varying wrist cable tensions. Further, the measured transverse forces are independent of both surgical and wrist friction induced torques applied distal to the combined groups of strain gauges. Finally, the measured forces along the x- and y-axes are independent of temperature changes when at thermal equilibrium over all gauges. This may be seen by adding an equal temperature disturbance strain to all four gauges in the equations for $F_x$ and $F_y$ and noting that the disturbances cancel. Thermal transients during which gauge temperatures are unequal are not compensated by this design although other measures may be taken to do so.

The measurements of the torques about the x- and y-axes (Tx and Ty) at the instrument tip are derived from the differences of the gauges paired across the shaft diameter and the sum of the pair differences along the shaft axis multiplied by a factor EI/4r, wherein once again E is the shaft material modulus of elasticity in the axial direction, I is the shaft section moment of inertia, and r is the radius from the shaft axis to the acting plane of the gauges. Thus the forces (Fx, Fy, Fz) and torques (Tx, Ty) exerted at the instrument tip are measured without errors due to wrist orientation or the location of a gripped tool such as a suture needle within jaws or tissue held in a grasper, for example. Torque measurements about the x- and y-axes are also independent of temperature at steady state. The calculations of the torques are derived from the following equations.

Figure 5:
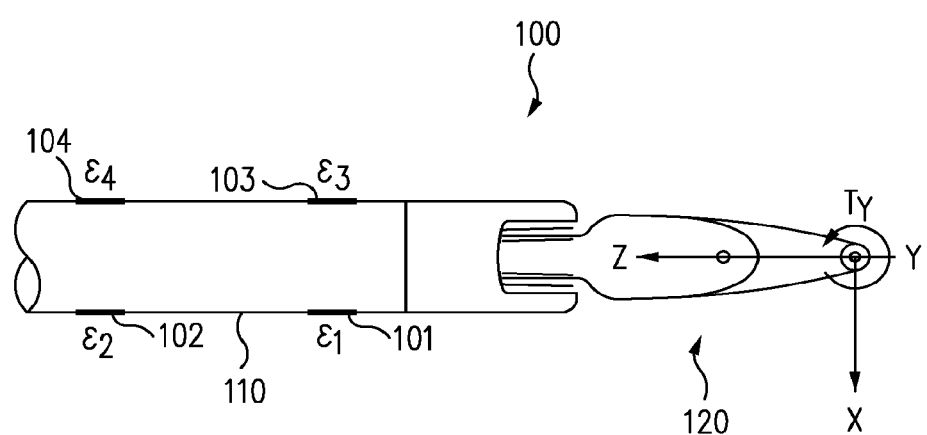
FIG. 5 is a second top view of the surgical instrument of FIG. 2 showing applied torque in accordance with the embodiment of the present invention.
Figure 6:
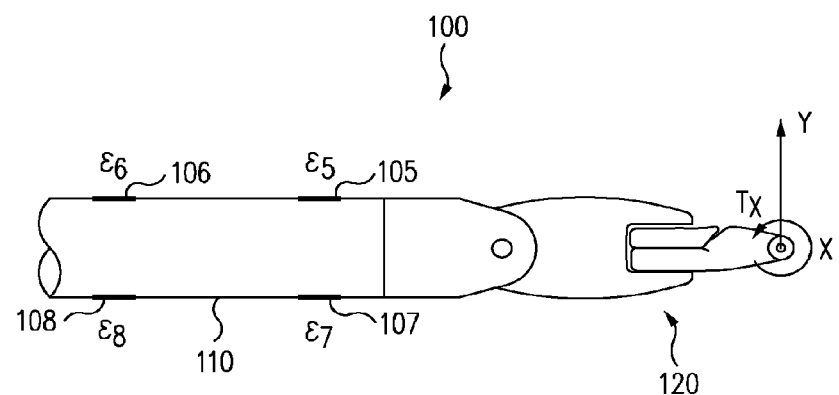
FIG. 6 is a second side view of the surgical instrument of FIG. 2 showing applied torque in accordance with the embodiment of the present invention.

With respect to FIGS. 5 and 6 in conjunction with FIG. 2, $$T_x \quad T_y$$

$$\begin{bmatrix} 0 \\ 0 \\ 0 \\ 0 \\ -1 \\ -1 \\ 1 \\ 1 \end{bmatrix} EI/4r \quad \begin{bmatrix} 1 \\ 1 \\ -1 \\ -1 \\ 0 \\ 0 \\ 0 \\ 0 \end{bmatrix} EI/4r$$

$$\sigma=Mr/I$$

$$\sigma_1=\sigma_2=Tr/I$$

$$E=\sigma/\epsilon => \epsilon=\sigma/E$$

$$\epsilon_1=\epsilon_2=Tr/EI$$

Thus, $$(\epsilon_1+\epsilon_2-\epsilon_3-\epsilon_4)EI/4r=T_y$$

$$(-\epsilon_5-\epsilon_6+\epsilon_7+\epsilon_8)EI/4r=T_x$$

While the invention described above may be applied to surgical instruments of many constructions, it is of particular value for use with anisotropic linear fiber reinforced polymer tubing, in one example, because all gauges are oriented parallel to the z-axis with constant and easily characterized elastic properties. Similar advantages may be gained with properly characterized woven reinforced tubing, and the method is also applicable to uniform elastic property tubing.

In one example, various strain gauges may be used, including but not limited to conventional foil type resistance gauges, semiconductor gauges, optic fiber type gauges using Bragg grating or Fabry-Perot technology, or others, such as strain sensing surface acoustic wave (SAW) devices. Optic fiber Bragg grating (FBG) gauges may be advantageous in that two sensing elements may be located along one fiber at a known separation, thereby only requiring the provision of four fibers along the instrument shaft.

As an example, with no intention to limit the invention thereby, two commercially available fiber strain gauge technologies noted above will be described in greater detail.

The first technology employs a Fabry-Perot cavity formed by first fusing two fibers together so as to produce a half-mirror at the junction and then polishing the tip of the fiber so as to form a full mirror. Light is sent into the fiber to generate reflections from both the half-mirror and the full mirror. The two reflections generate interference patterns that are a function of the distance between the two mirrors, thus allowing the strain in the fiber to be sensed. This Fabry-Perot technology is commercially available from FISO Technologies, Inc. of Quebec, Canada, with more information available at http://www.fiso.com.

The second technology uses a Bragg grating written into the fiber with a UV laser. The fiber Bragg grating (FBG) gauge comprises a spatial periodicity in the refractive index along the axis of the fiber. Light entering the FBG is preferentially reflected at a particular wavelength (the Bragg wavelength) that is a function of the period of the index variation. Other wavelengths pass through the FBG unchanged. To measure strain, broad spectrum IR light is sent down the fiber, and the wavelength of the reflection indicates the strain. This FBG technology is commercially available from Smart Fibres Ltd. of Bracknell, England, with more information available at http://www.smartfibres.com.

Multiple FBGs can be written into a fiber if they are formed in such a way as to use a different range of wavelengths, and as noted above, this is a particularly useful property for the double ring of strain gauges embodiment because only four fibers would need to be embedded into the instrument shaft, each with two FBGs separated by a known distance. To implement the double ring arrangement of strain gauges with the Fabry-Perot technology, eight fibers would be required.

Both fiber technologies require an interrogator unit that decodes the optically encoded strain information into electrical signals compatible with the computer control hardware of the robotic surgical system. A processor may then be used to calculate forces according to the equations outlined above in conjunction with the signals from the strain gauges/sensors. In one embodiment, an interrogator unit 170 (FIG. 9A) is mounted on the manipulator, or elsewhere in the surgical system, which may require routing of the optical fiber across the sterile boundary. In one case, an optical coupling is incorporated into the standard instrument interface with the manipulator such that installation of an instrument onto the manipulator automatically forms an optical link with the instrument. Advantageously, this avoids the need to carry external cabling to the instrument. In a second case, a fiber pigtail exits the top of the instrument for mating with a connector presented on the manipulator but not part of the instrument interface. In these two cases, the interrogator may be built into the manipulator or fiber cables may run through the manipulator to an interrogator mounted on the surgical system or in the operating room separate from the manipulator. In a third case, a fiber pigtail exits the top of the instrument without passing through the manipulator for mating with an interrogator unit mounted in the operating room separate from the manipulator, which has the benefit of not requiring connection of the fiber cable when the instrument is attached or removed from the manipulator.

Other combinations of gauge orientations, numbers of gauges, and outputs are also within the scope of the present invention. In accordance with another embodiment of the present invention, a useful simplification of the two ring eight gauge arrangement is to remove one of the rings of gauges. This simplification removes the ability to distinguish between forces and moments on a given axis (e.g., x or y), but many items in the surgical environment (e.g., human tissue, sutures) do not support moments well, and thus it is possible to assume that all strain information is from x- and y-axis forces. In a further embodiment, three gauges 120 degrees apart may be used to form a set instead of four gauges 90 degrees apart. Thus, combinations of gauges may include a single ring of three gauges 120 degrees apart, two rings of three gauges each 120 degrees apart (i.e., a total of six gauges), a single ring of four gauges 90 degrees apart, and two rings of four gauges each 90 degrees apart (i.e., a total of eight gauges). Single ring gauge embodiments may be useful for non-wristed tools such as probes. Gauges may also be oriented on the surface of shaft 110 at angles that permit recovery of the additional torque signal $T_z$ about the shaft axis. However, the off-axis elastic properties of the shaft must be taken into account.

In accordance with yet another embodiment of the present invention, x- and y-axis forces may be detected with sensor(s) at the distal end of the instrument shaft as disclosed above, and z-axis forces may be detected with a sensor(s) located outside of the body near the proximal end of the instrument. Various sensors may be used outside of the body for detecting z-axis forces, including but not limited to strain gauges and/or fiber technologies.

Typically, z-axis forces cannot be easily sensed at the instrument tip because the instrument shaft is subject to significant internal forces in the z-direction from the internal cabling necessary for transmitting torques to the instrument pitch and yaw axes. These cables run inside the instrument shaft, and experiments have shown that the compression loads on the shaft vary significantly as the instrument is operated. Attempts to sense z-direction strain with gauges on the instrument shaft will include a significant cable actuation "noise" in addition to the applied z-axis force of interest. Thus, it is preferred that z-axis forces be sensed in a location substantially not subject to internal cabling forces. It is noted that these cables also impart some x- and y-moments at the base of the shaft because the cables are not completely centered and because cable tension on either side of the wrist pulleys will vary as the wrist is operated. However, experiments have shown that, unlike the z-direction cable forces, these variations are relatively small compared to the expected externally applied forces.

Z-axis forces may be detected outside the body with relative accuracy with mainly the cannula seal friction and sliding friction of the shaft in the cannula adding "noise" to the signal of interest. In one embodiment, cannula seals are disposable and may be packaged with friction reducing lubrication or a friction reducing coating (such as Parylene) which is bonded to the cannula seal surfaces. In another embodiment, the instrument shaft surfaces may be treated with a friction reducing coating (e.g., PTFE) to negate undesirable friction noise. Both friction reducing methods may also be used simultaneously.

A sensor may be placed in various locations outside of the body proximate the proximal end of the surgical instrument in accordance with the present invention. It is preferred that the sensor be built into the manipulator rather than the disposable instrument, but this is not necessary. In one embodiment, a sensor(s) 160 (FIG. 9A) may be positioned at mount points for the instrument sterile adaptor on the manipulator arm insertion (z-axis) carriage (e.g., on a carriage link which is described in greater detail below). In another embodiment, a sensor(s) may be placed at the instrument backplate. This would be substantially equivalent to placing sensors on the sterile adaptor mount points but would require an additional sensor be built into every instrument.

By contrast to the z-axis forces, the x- and y-axis forces cannot easily be sensed outside the body because of contact with the cannula which in turn is subject to the large patient body wall forces and torques imparted at the remote center that mask the comparatively small x- and y-axis tissue contact forces. Thus, it is preferred that x- and y-axis forces be sensed in a location substantially not subject to body wall forces or torques such as the distal end of the instrument shaft proximal to the instrument wrist joint as discussed above. In the disclosure above, a force-torque sensor integrated with the tubular distal end of an endoscopic surgical instrument shaft is described. In one embodiment, the sensor comprises two sets of four strain gauges located about the periphery of the shaft such that the members of a group of four are 90 degrees apart around the shaft and the two groups of four are a distance 1 apart along the shaft. In one aspect, it was desired to determine the side load (e.g., $F_y$) on the instrument tip or jaws. The disclosure explains that by computing the bending moment at each group of sensors due to the side load and then subtracting the two values, a measure of the side load independent of wrist orientation and resulting effective lever arm length can be derived. A concern is that the moments applied to the distal end of the shaft by the actuation of the instrument wrist axes and transmitted to the shaft by the friction in the wrist pivots will interfere with the intended measurement of the side loads. However, by carrying the terms due to such moments through the arithmetic governing the measured strains, it may be seen that the terms due to such moments drop out when the side load forces are calculated.

Figure 7:
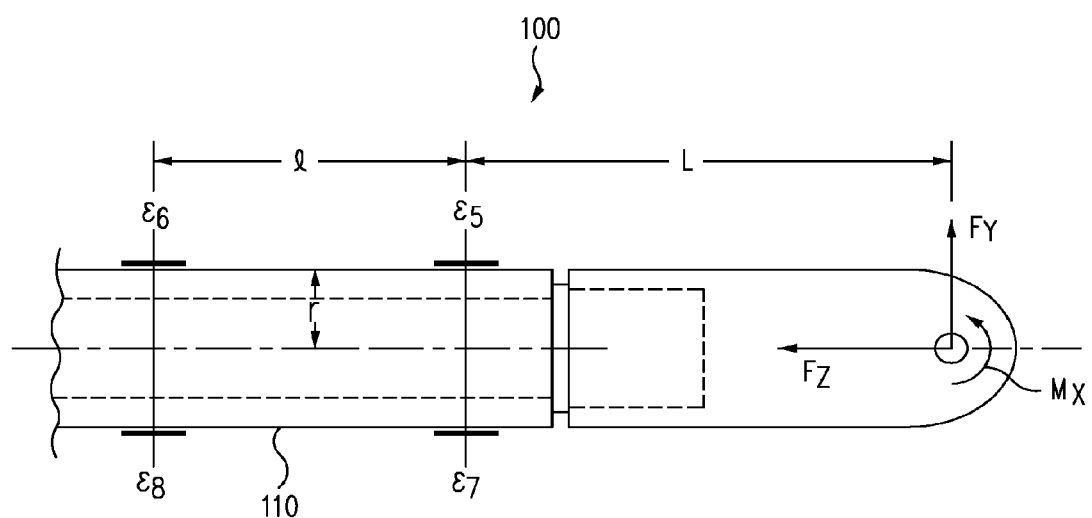
FIG. 7 shows a free body diagram of the instrument shaft and proximal wrist clevis subjected to loads and moments applied by the wrist mechanism in accordance with an embodiment of the present invention.
Figure 8:
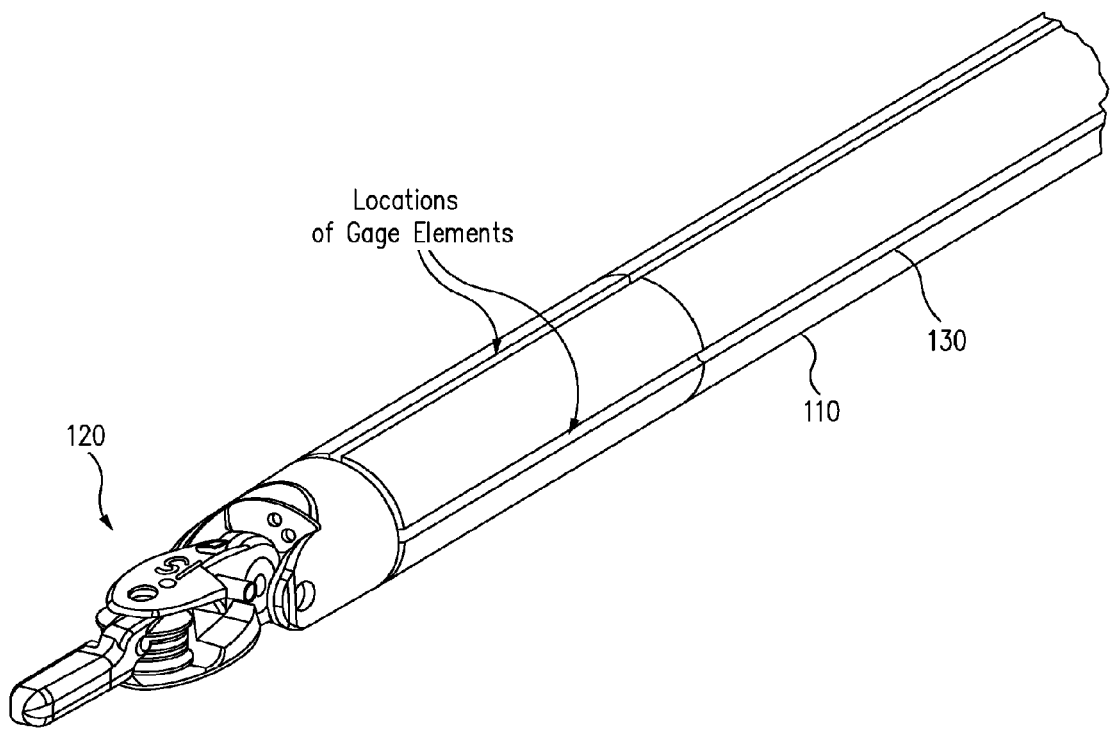
FIG. 8 shows a grooved instrument shaft for embedded strain gauges in accordance with an embodiment of the present invention.

Referring now to FIG. 7 and the equations below, by proper arithmetic combination of the strains sensed by the eight strain gauges, it is possible to eliminate the unwanted axial wrist cable forces and wrist actuation torques while preserving the desired side load forces. FIG. 7 illustrates a free body diagram of the shaft subjected to loads and moments applied by the wrist mechanism. A variety of forces and moments may apply to the free body of the outboard wrist 120 (FIG. 6). Depending on the combination of tip loads, cable loads, and motion and acceleration of the wrist, the forces and moment applied to the end of the shaft 110 viewed in the y-z plane of the shaft reduce to $F_y$ (side load), $F_z$ (axial load), and $M_x$ (wrist pivot friction moment load).

Therefore, one can express the strains $\epsilon_5$, $\epsilon_6$, $\epsilon_7$, and $\epsilon_8$ on the four gauges in this plane in terms of these three loads and derive the expression for the desired side force $F_y$ as follows.

Tensile strain>0
Compressive strain<0

$$\epsilon_7 = -F_z/EA + M_x r/EI + F_y Lr/EI$$

$$\epsilon_5 = -F_z/EA - M_x r/EI - F_y Lr/EI$$

$$\epsilon_8 = -F_z/EA + M_x r/EI + F_y(1+L)r/EI$$

$$\epsilon_6 = -F_z/EA - M_x r/EI - F_y(1+L)r/EI$$

$$[(\epsilon 8 - \epsilon 6) - (\epsilon 7 - \epsilon 5)] = -F_z/EA[(1-1)-(1-1)] +$$
$$M_x r/EI[(1-(-1))-(1-(-1))] +$$
$$F_y r/EI\{[(1+L)-(-(1+L))]-[L-(-L)]\}$$
$$= 2lF_y r/EI$$

Therefore, $$F_y = [(\epsilon_8 - \epsilon_6) - (\epsilon_7 - \epsilon_5)]EI/2lr$$

$M_x$ and $F_z$ do not appear.

As can be seen, the strains due to the moment load $M_x$ which are felt identically on both sets of gauges drop out, leaving the moment loads due to the applied side force $F_y$. The strain components due to the axial force $F_z$, also felt identically on both sets of gauges, also drop out. Therefore, since the wrist actuating torques are transmitted to the shaft carrying the strain sensors by the friction in the wrist joint, they result in moment loads that cancel when the signals from the two sets of sensors are subtracted, leaving a relatively clean signal due to the side force load alone as desired. The above disclosure similarly applies to $\epsilon_{1-4}$ in the x-z plane with x and y interchanged.

Calculating a clean signal due substantially to the side force load alone advantageously eliminates the need to place the sensor outboard of (distal to) the wrist joints as previously done to eliminate the wrist friction moments. The present invention thus avoids the need to route wires or optic fibers associated with the strain gauges through the flexing wrist joint. Furthermore, the yaw and grip axes may be accomplished on the same pivot axis rather than having them separate as previously done.

For all of the methods and apparatus mentioned above, it may be advantageous to use a calibration process in which forces and torques are applied to the instrument tip serially, simultaneously, or in combinations while correction factors and offsets are determined to apply to the theoretical equations described above for combining the gauge outputs to obtain $F_x$, $F_y$, $F_z$, $T_x$, and $T_y$. Calibration may be accomplished either by directly calculating the correction factors and offsets or by a learning system such as a neural network embedded in the calibration fixture or in the instrument itself. In any calibration method, the calibration data may be programmed into an integrated circuit embedded in the instrument so that the surgical system using the individual instrument can correctly identify and apply its correction factors and offsets while the instrument is in use.

Figure 9A:
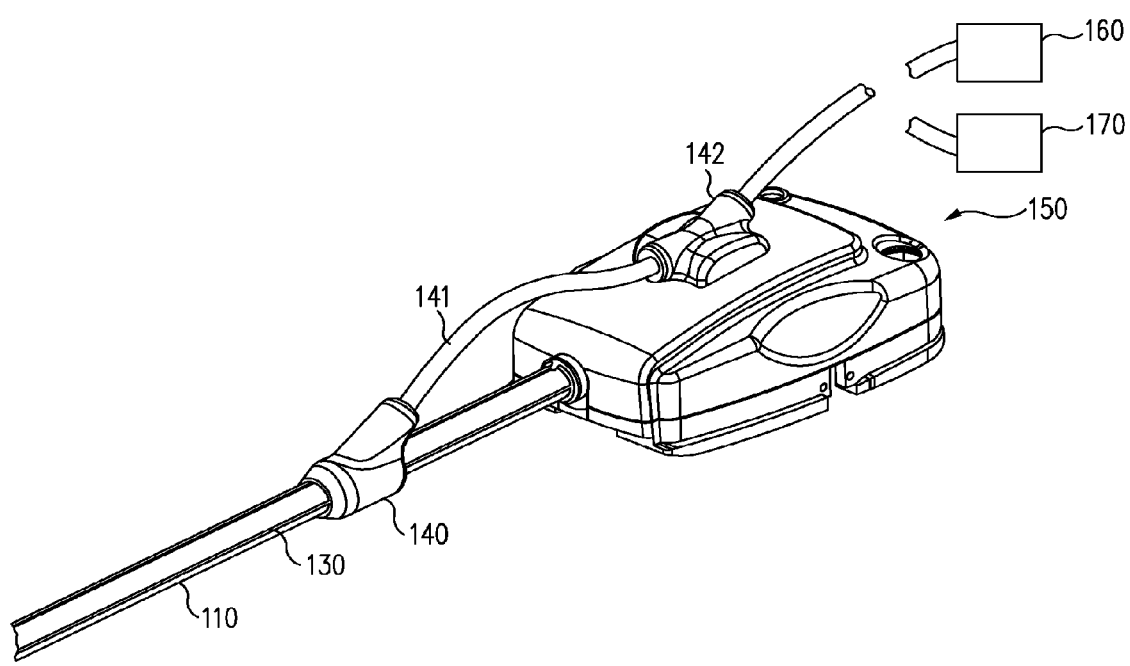
FIGS. 9A-9C show different configurations of a strain relief and service loop for strain gauge wires or optic fibers in accordance with an embodiment of the present invention.
Figure 9B:
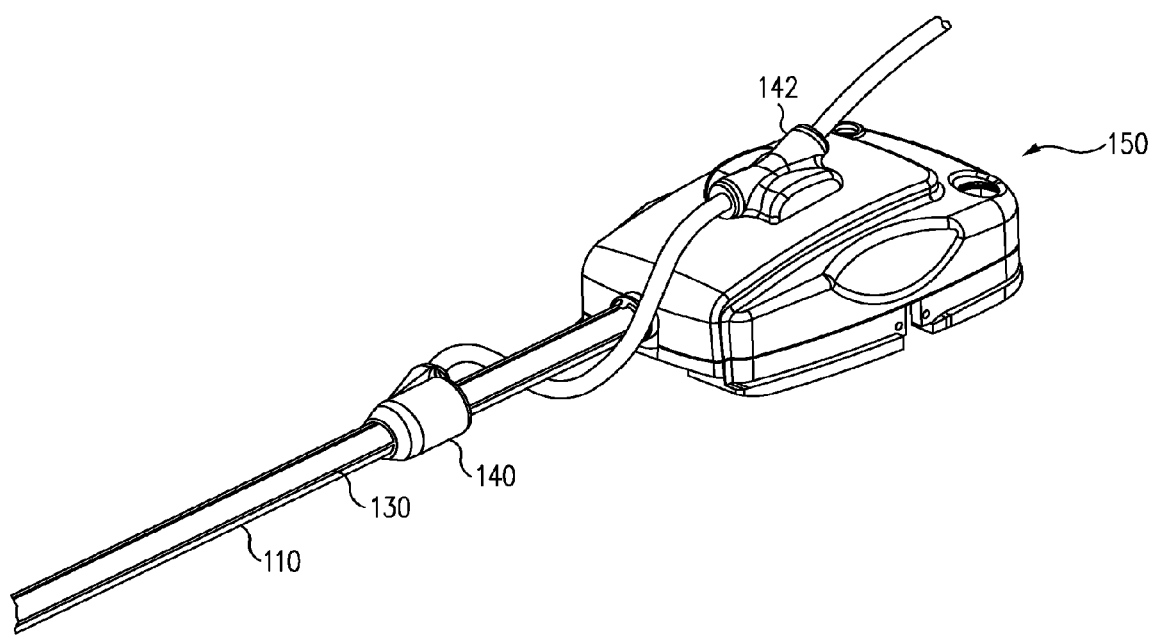
Figure 9C:
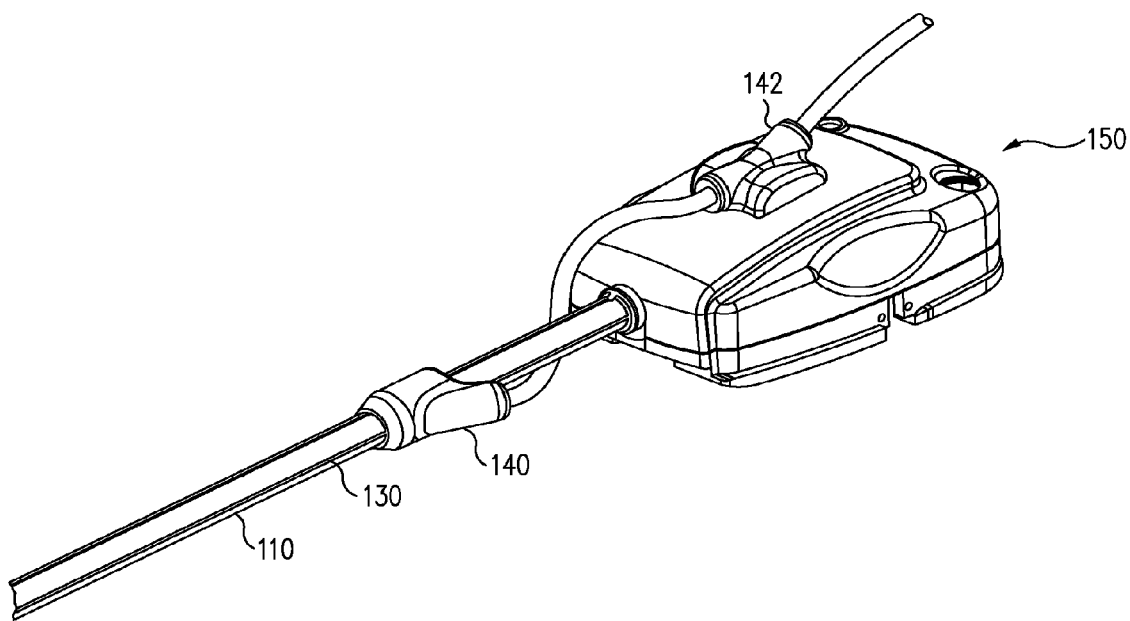
Figure 10:
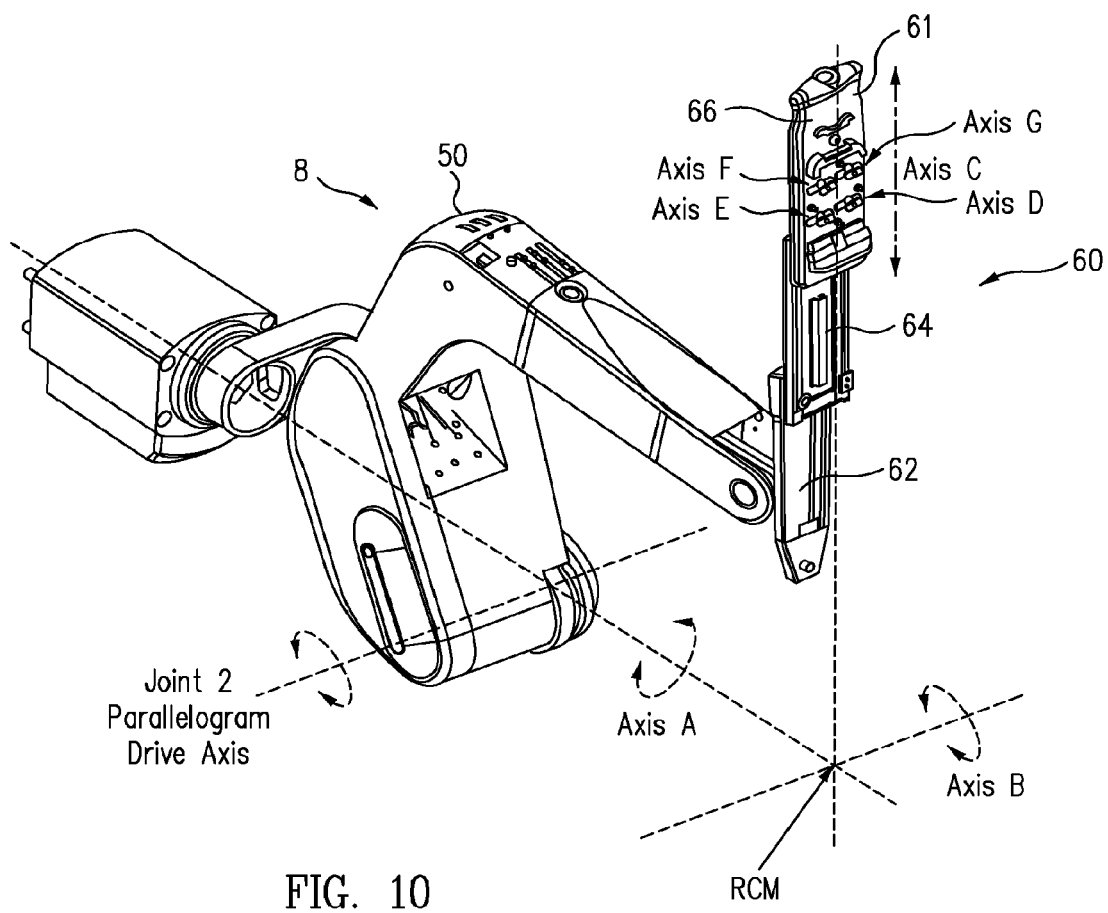
Figure 11A:
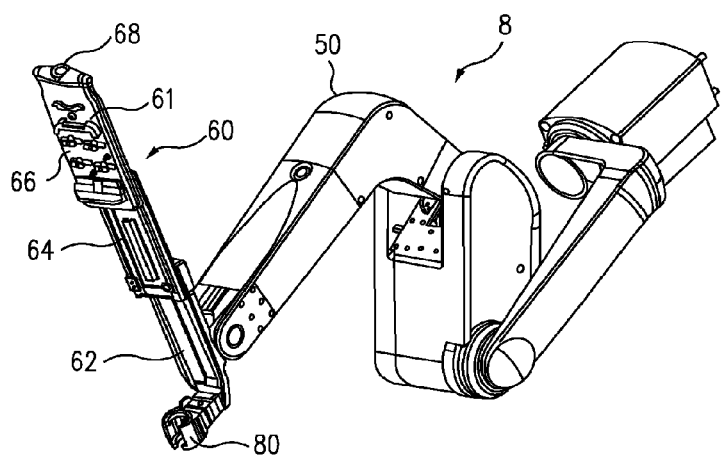
Figure 11B:
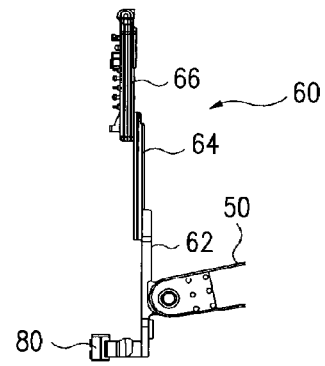
Figure 12A:
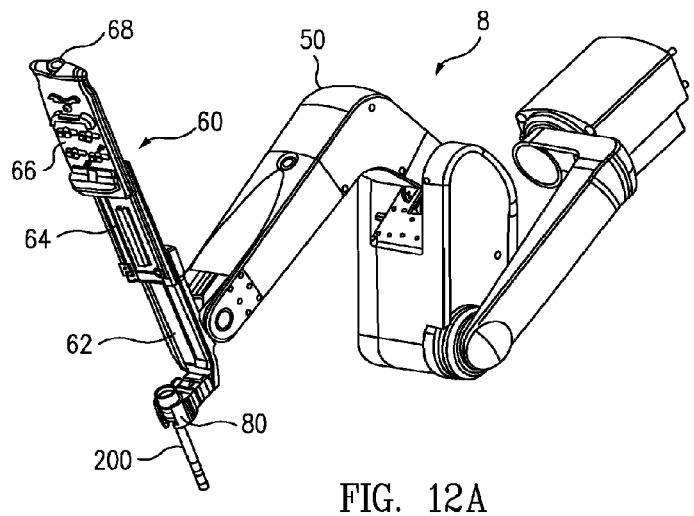
Figure 12B:
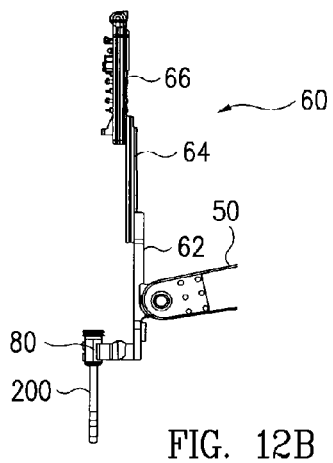

Optical fibers embedded in the instrument shaft preferably should exit the shaft near the proximal end of the instrument in a way that does not impede rotation of the shaft relative to the instrument housing/carriage while preserving the physical integrity of the fiber. Referring now to FIGS. 8 and 9A-9C, in accordance with an embodiment of the present invention, Fabry-Perot or FBG sensing elements may be embedded in shallow grooves 130 just below the shaft 110 surface near the instrument shaft distal tip just behind the wrist clevis, and then epoxied or otherwise potted into place. Grooves 130 may lead back toward the proximal end of the instrument, which includes the motion inputs and wrist cable actuator mechanism (the "housing") 150. Grooves 130 may be formed in the shaft during the initial pultrusion process, or the grooves may be machined after shaft production. At a point near the proximal mechanism or housing, the fibers may be routed out of the grooves at a gentle angle and bundled through a strain relief 140 into a protective flexible sheath 141 which would carry the optical fibers to a strain relieved anchor point 142 on the top cover of the mechanism housing 150. The flexible sheath 141, strain relief 140, and anchor point 142 should have sufficient length and flexibility to permit safe repeated flexing and torsion as the instrument shaft 110 is rotated, as shown in FIGS. 9A-9C.

In another embodiment, if the instrument shaft is made with resin and fiber (e.g., fiberglass or carbon fiber), the optical fibers may be woven or embedded with linear axial reinforcing fibers at the desired angular (90 or 120 degrees) and radial (near surface) positions into the instrument shaft fiber matrix prior to the application of resin.

As noted above, z-axis forces may be detected outside the body with relative accuracy, with mainly the cannula seal friction and sliding friction of the shaft in the cannula adding "noise" to the signal of interest. In accordance with one embodiment of the present invention, a cannula, a cannula seal, and/or an instrument are provided for reducing friction to substantially reduce noise when determining z-axis forces.

Referring now to FIGS. 10-14B, perspective views and respective side views of a manipulator 8 including a manipulator arm 50 and a telescopic insertion axis 60 with the coupling of a cannula 200 and an instrument 100 are shown in accordance with an embodiment of the present invention.

Telescopic insertion axis 60 includes a first link or base link 62, a second link or idler link 64 operably coupled to base link 62, and a third link or carriage link 66 operably coupled to idler link 64. Some of the manipulators include a telescopic insertion axis 60 in accordance with an embodiment of the present invention, although in other embodiments, the manipulators may include a linear sliding carriage or a telescopic insertion axis 60. Telescopic insertion axis 60 allows for movement of mounted tool or instrument 100, via three operably coupled links, with improved stiffness and strength compared to previous designs, a larger range of motion, and improved dynamic performance and visibility proximate the surgical field for system users (in addition to other advantages), as is described in greater detail in pending U.S. application Ser. No. 11/613,800, filed Dec. 20, 2006, which is incorporated by reference herein for all purposes.

Base link 62 is operably coupled to a distal end of manipulator arm 50, and in one example has an accessory clamp 80 attached to a distal end of base link 62. A cannula 200 may be mounted onto accessory clamp 80. An example of applicable accessory clamps and accessories are disclosed in pending U.S. application Ser. No. 11/240,087, filed Sep. 30, 2005, the full disclosure of which is incorporated by reference herein for all purposes. An example of applicable sterile adaptors and instrument housings are disclosed in U.S. application Ser. No. 11/314,040, filed Dec. 20, 2005 and in U.S. application Ser. No. 11/395,418, filed Mar. 31, 2006, the full disclosures of which are incorporated by reference herein for all purposes.

Carriage link 66 includes an instrument interface for operably coupling (e.g., electrically and/or physically) to an instrument sterile adaptor (ISA) 70 (FIGS. 13A-13B), which is capable of operably coupling (e.g., electrically and/or physically) to a housing of an instrument (e.g., housing 150 of FIGS. 14A and 14B), and controls the depth of the instrument inside a patient. In one embodiment, the sterile adaptor is integrated with a drape that may be draped over the robotic surgical system, and in particular the manipulator system, to establish a sterile barrier between the non-sterile manipulator arms (e.g., a patient side manipulator as further described below) and the sterile field of the surgical procedure. An example of an applicable drape and adaptor is disclosed in pending U.S. application Ser. No. 11/240,113, filed Sep. 30, 2005, the full disclosure of which is incorporated by reference herein for all purposes. An example of an instrument interface is disclosed in pending U.S. application Ser. No. 11/613,695, filed Dec. 20, 2006, the full disclosure of which is incorporated by reference herein for all purposes.

Idler link 64 is movably coupled between base link 62 and carriage link 66 to allow the links 62, 64, and 66 to move relative to one another along a lengthwise axis in a telescoping fashion. In one embodiment, base link 62 has a narrower form factor than idler link 64, and idler link 64 has a narrower form factor than carriage link 66, thus providing for greater visibility near the surgical field.

For convenience, a manipulator such as manipulator 8 that is supporting a surgical tool used to manipulate tissues is sometimes referred to as a patient-side manipulator (PSM), while another manipulator which controls an image capture or data acquisition device such as an endoscope may be referred to as an endoscope-camera manipulator (ECM). The manipulators may optionally actuate, maneuver and control a wide variety of instruments or tools, image capture devices, and the like which are useful for surgery.

Instruments 100 may be manually positioned when setting up for a surgical procedure, when reconfiguring the manipulator system for a different phase of a surgical procedure, when removing and replacing an instrument with an alternate instrument, and the like. During such manual reconfiguring of the manipulator assembly by an assistant, the manipulator assembly may be placed in a different mode than is used during master/slave telesurgery, with the manually repositionable mode sometimes being referred to as a clutch mode. The manipulator assembly may change between the tissue manipulation mode and the clutch mode in response to an input such as pushing a button or switch on manipulator 8 (e.g., a clutch button/switch 68 in FIGS. 11A-14A), or some other component to the manipulator assembly, thereby allowing the assistant to change the manipulator mode.

Figure 15:
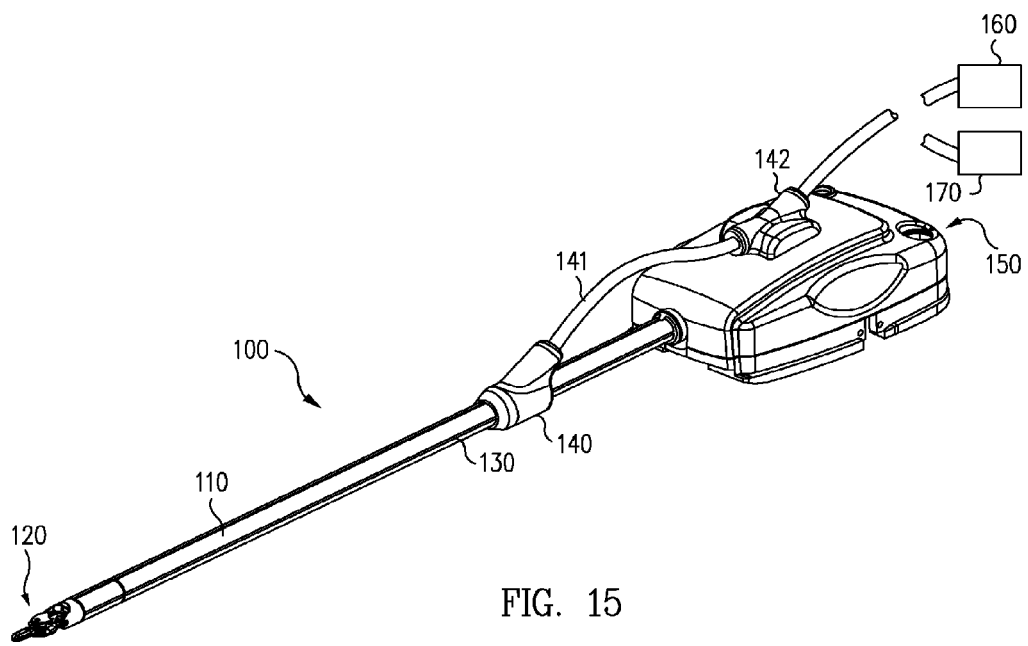
FIG. 15 shows an instrument in accordance with an embodiment of the present invention.

Referring now to FIG. 15, a perspective view of instrument 100 is illustrated. In one embodiment, the exterior of instrument shaft 110 includes surfaces treated with a friction reducing coating (e.g., polytetrafluoroethylene (PTFE), Parylene, or polyamide) and/or is comprised of friction reducing materials to negate undesirable friction noise. Shaft 110 may be of a uniform diameter covering strain gauges positioned in grooves along the instrument shaft as described above such that the entire shaft of the instrument may pass through a cannula and/or a cannula seal with minimal friction or snagging.

Figure 16A:
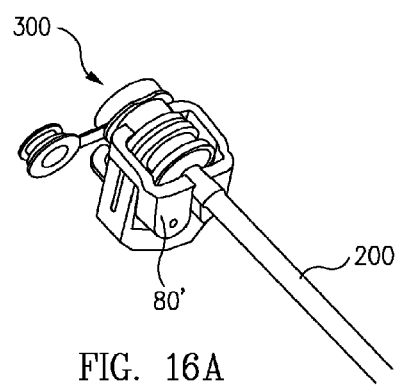
FIGS. 16A and 16B illustrate a front and a back perspective view of a cannula and a cannula seal assembled together in accordance with an embodiment of the present invention.
Figure 16B:
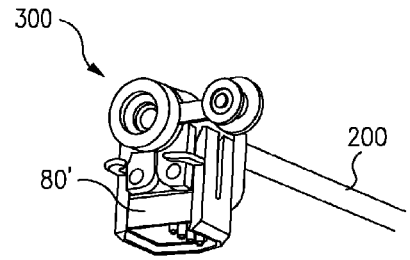

Referring now to FIGS. 16A and 16B, front and back perspective views are illustrated of cannula 200 and cannula seal 300 assembled together and mounted on an accessory clamp 80' in accordance with an embodiment of the present invention.

Figure 17A:
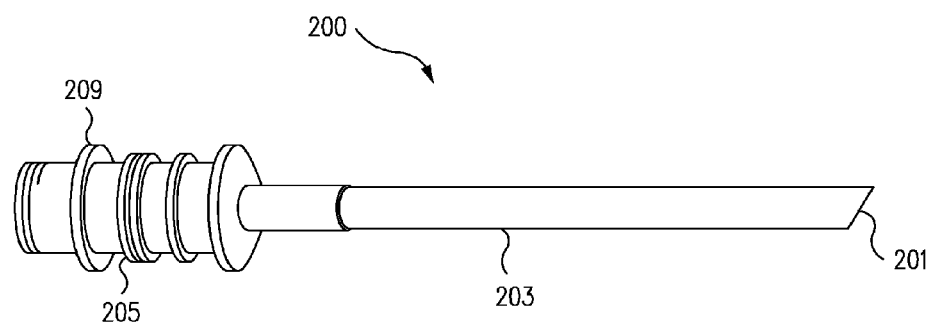
FIGS. 17A and 17B illustrate a perspective view and a cross-sectional view of a cannula in accordance with an embodiment of the present invention.
Figure 17B:
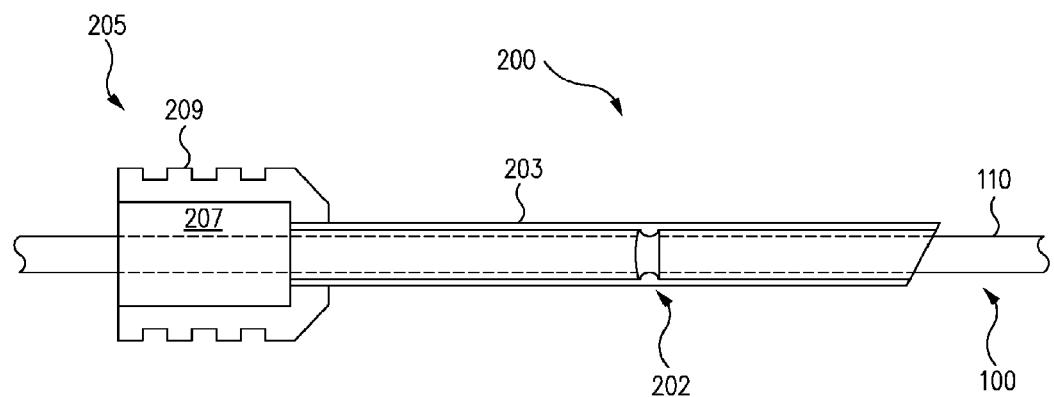

Referring now to FIGS. 17A and 17B, a perspective view and a cross-sectional view of cannula 200 are illustrated. In one embodiment, cannula 200 includes a proximal portion 205 that is coupled to a manipulator (such as with an accessory clamp 80 or 80'), a tube 203, a distal portion 201, and an annular rib 202 within tube 203 that makes guiding contact with an inserted instrument shaft 110 (shown by dashed and solid lines). Proximal portion 205 includes exterior ridges 209 and an interior space 207 for receipt of a rubber portion and a seal lip of a cannula seal (see e.g., FIGS. 18A and 18B) as described in more detail below. In one example, tube 203 is comprised of stainless steel, and an interior surface of tube 203 may be coated or lined with a lubricating or anti-friction material, such as Parylene.

Annular rib 202 may be formed individually (e.g., as an inserted ring part) or as a part of tube 203, and rib 202 may also be comprised of or coated with anti-friction material, such as polytetrafluoroethylene (PTFE), polyetheretherketone (PEEK), polyethylene terephthalate (PET), Parylene, or polyamide. Rib 202 is preferably comprised of a material that is able to withstand high temperatures, auto-clavable, and durable.

In one embodiment, rib 202 is positioned along tube 203 to reduce or prevent interference or contact of a wrist of instrument 100 with the distal portion 201 of cannula 200 taking into consideration the deflection of instrument shaft 110 upon a side load. In one example, rib 202 is positioned about 3 inches from distal portion 201 of cannula 200 with the inner diameter of tube 203 being about 0.335 inches and the instrument shaft having an outer diameter of about 0.32 inches. In a further example, annular rib 202 may be placed along an axial position of the cannula tube 203 proximate to a force sensor on instrument shaft 110 measuring side loads at or near the instrument tip. Thus, rib 202 reduces or eliminates local contact of tube 203 with instrument shaft 110 thereby avoiding interfering contact of the cannula to instrument force sensors. In another example, rib 202 may be positioned to localize and make a predictable contact location between instrument shaft 110 and a cannula ID without touching an instrument force sensor. In yet another example, annular rib 202 may be placed so as to coincide with a location in which the cannula passes through a patient body wall or the remote center of rotation or motion (RCM) of the manipulator arm.

Figure 18A:
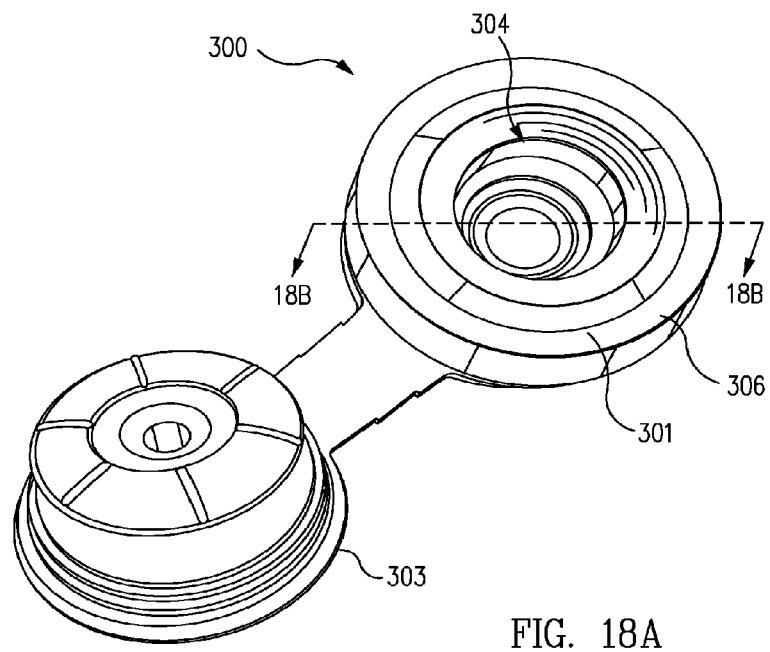
FIGS. 18A and 18B illustrate a perspective view and a cross-sectional view of a cannula seal including a symmetric seal lip in accordance with an embodiment of the present invention.
Figure 18B:
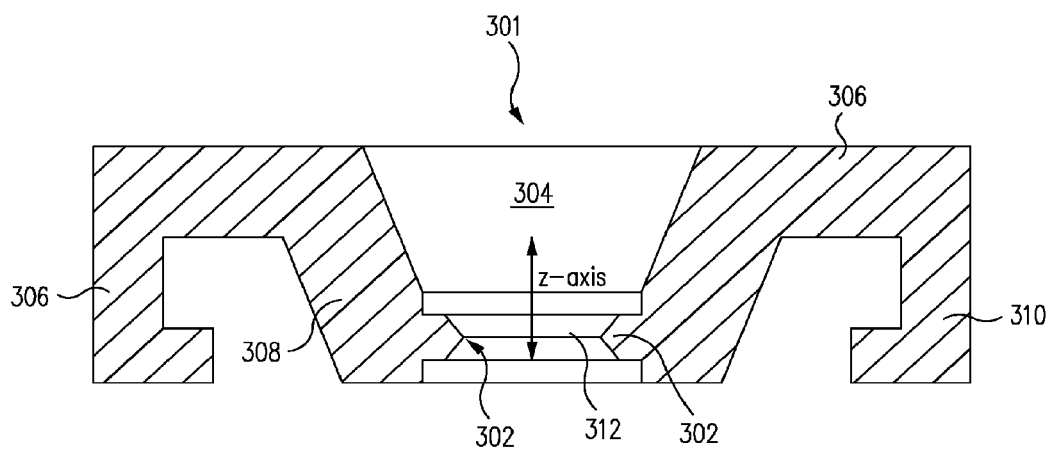

Referring now to FIGS. 18A and 18B in conjunction with FIGS. 17A and 17B, a perspective view and a sectional view along line 18B-18B of a cannula seal 300 are respectively illustrated. In one embodiment, cannula seal 300 includes a seal 301 and an optional size adapter 303 that fits into seal 301. Seal 301 includes a molded silicone rubber portion 306, an aperture 304 at the center of the rubber portion 306, and a seal lip 302 in the interior of aperture 304. Rubber portion 306 is shaped to operably couple to proximal portion 205 of cannula 200 such that aperture 304 and seal lip 302 are placed substantially within aperture 207 of cannula 200. In one example, rubber portion 306 is shaped substantially as a tapered tube 308 with an overhang 310 that fits over or snaps onto an exterior ridge 209 of proximal portion 205. Adapter portion 303 fits into aperture 304 to reduce the diameter of an instrument pathway through the cannula seal for smaller endoscopic instruments. Adapter portion 303 may also include a similar seal lip to that further described below. Cannula seal 300 may further include an acrylic plug on a flap over the aperture.

Seal lip 302 seals against an instrument shaft (e.g., shaft 110) of instruments being inserted through cannula 200, and in one example, seal lip 302 is comprised of an elastomer material such as silicone rubber with an anti-friction coating such as Parylene. Seal lip 302 also has a geometry to reduce direction dependent friction in accordance with the present invention. In one embodiment, seal lip 302 has a symmetrical design about a plane perpendicular to the z-axis to equalize friction in both directions of instrument movement along the z-axis and so as to be non- or minimally self-actuating. In one example, seal lip 302 is a tapered protrusion radiating toward the center of tapered tube 308 and is symmetric about a plane perpendicular to the z-axis (e.g., at plane 312). In another example, seal lip 302 may be designed for precise desired tightness of contact with specific instrument diameters.

Figure 19:
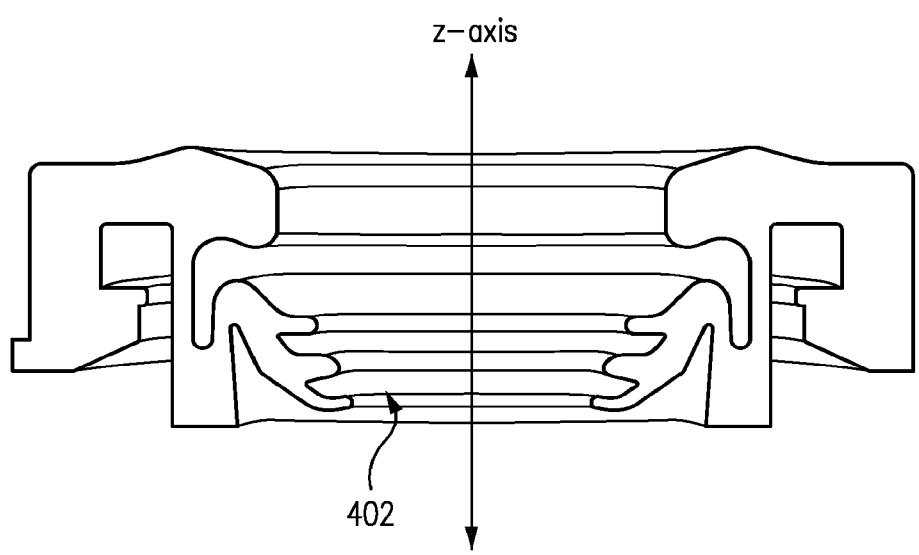
FIG. 19 illustrates a cross-sectional view of a cannula seal including an asymmetric seal lip.

In contrast, FIG. 19 illustrates an asymmetric seal lip 402 which is shaped to curve in an upward direction along the z-axis and is therefore asymmetric about a plane perpendicular to the z-axis.

Advantageously, the present invention provides for reducing friction to substantially reduce noise or other interference when determining z-axis forces from outside the body. The present invention further eliminates undesirable interference from wrist actuator cable tensions ($F_z$) and wrist actuation moments ($M_x+M_y$) with the desired sensing of the tip side load ($F_x+F_y$) by combining strain measurements and locating the sensors inboard of the wrist pitch and yaw axes. Accordingly, wires or optic fibers are not required to pass through the wrist joints, thereby avoiding possible signal loss, breakage of wires or fibers, interfering noise, and/or current leakage (fiber optics do not require current and provide no leakage path) while insuring greater reliability and simpler less expensive construction. The use of fiber strain gauges advantageously provides immunity to electrical and magnetic fields, which become an issue with cautery tools that use large currents and voltages, while also providing bio-compatibility, durability to withstand temperatures and pressures associated with autoclaving, and size advantages. Furthermore, the wrist yaw and grip axes may share the same pivot shaft and actuator cables operated differentially for yaw and in common mode for grip thus simplifying and reducing the cost of the assembly while increasing its reliability. In addition, the combined overall length of the wrist and end effector may be kept to a minimum, thus reducing the side offset distance when the wrist is bent.

Embodiments described above illustrate but do not limit the invention. It should also be understood that numerous modifications and variations are possible in accordance with the principles of the present invention. For example, the various features for reducing friction when determining z-axis forces may be used individually or in various combinations. Furthermore, the number of strain gauges and their configuration may vary but must allow for applicable force and torque determinations. In yet another example, strain gauges may be non-uniformly offset in a ring, such as by 60/120/60/120 degrees or by 70/110/70/110 degrees. Accordingly, the scope of the invention is defined only by the following claims.

We claim:

1. A cannula, comprising:
   a proximal portion including an opening and a distal end, the opening of the proximal portion being configured to receive an instrument shaft, and the proximal portion being configured to operably couple to a manipulator arm;
   a tubular member extending from the distal end of the proximal portion, the tubular member including an inner surface and an opening, the opening of the tubular member being configured to receive the instrument shaft; and
   an annular rib extending radially inward from the inner surface of the tubular member.

2. The cannula of claim 1, wherein the annular rib is positioned within the tubular member to prevent contact between a force sensor on the instrument shaft and a distal end of the cannula.

3. The method of claim 2:
   wherein the rib is aligned radially on the inner surface of the cannula.

4. The cannula of claim 1, wherein the annular rib includes an anti-friction surface.

5. The cannula of claim 4, wherein the anti-friction surface comprises an acetal, a polyetheretherketone, a polyethylene terephthalate, a polytetrafluoroethylene, a Parylene, a polyamide, or a polyethylene.

6. A method comprising:
   sensing an axial force applied to a lengthwise axis of a shaft of a robotic surgical instrument,
      wherein the shaft is received proximally to distally within a cannula,
      wherein the sensing of the axial force is done by a force sensor positioned proximal to the cannula, and
      wherein the shaft comprises an antifriction outer surface; and
   reducing signal noise in the sensing of the axial force by sliding the antifriction outer surface of the shaft on an antifriction surface within the cannula.

7. The method of claim 6, wherein the antifriction surface within the cannula comprises an annular rib positioned to coincide with a position where the cannula passes through body tissue.

8. The method of claim 6, wherein the antifriction surface within the cannula comprises an annular seal having an anti-friction surface within a proximal portion of the cannula.

9. The method of claim 6, wherein the force sensor is mounted at an interface of the instrument housing with a manipulator arm.

10. The method of claim 6, wherein sliding the antifriction outer surface of the shaft on the antifriction surface within the cannula comprises sliding the outer surface of the shaft on an annular rib.

11. The method of claim 6, wherein sliding the antifriction outer surface of the shaft on the antifriction surface within the cannula comprises sliding the outer surface of the shaft on an anti-friction surface of a seal of the cannula.

12. A force sensing method comprising:
   sliding a robotic surgical instrument shaft through a cannula, wherein an outer surface of the instrument shaft includes an antifriction surface, wherein an inner surface of the cannula includes an antifriction surface, and wherein sliding the instrument shaft through the cannula includes sliding the antifriction surface of the outer surface of the instrument shaft against the antifriction surface of the inner surface of the cannula; and during the sliding of the surgical instrument shaft through the cannula, sensing a force applied in a lengthwise direction to the shaft.

13. The method of claim 12:

wherein the inner surface of the cannula includes a raised rib; and wherein the sliding of the instrument shaft through the cannula includes sliding the outer surface of the shaft against the rib.

14. The method of claim 13:

wherein the rib includes the antifriction surface of the inner surface of the cannula.

15. The method of claim 12:

wherein the antifriction surface of the inner surface of the cannula is a surface of a seal of the cannula.

16. A method of reducing signal noise in a force sensor positioned at a proximal end of a robotic surgical instrument shaft and positioned to sense a force applied lengthwise along the surgical instrument shaft, the method comprising:

sliding an outer surface of the instrument shaft against a radial rib of an inner surface of a cannula.

* * * * *